United States Patent
Takahashi et al.

(10) Patent No.: US 9,925,119 B2
(45) Date of Patent: Mar. 27, 2018

(54) DIALYSATE EXTRACTION DEVICE WITH PROJECTED COLLECTION PORT, MOUNTED WALL PART AND ATTACHABLE CONNECTION MEMBER

(71) Applicant: Nikkiso Company Limited, Tokyo (JP)

(72) Inventors: Masahiro Takahashi, Shizuoka (JP); Yusuke Nakano, Shizuoka (JP); Fumihiko Ishizaki, Shizuoka (JP); Hachiro Edamura, Shizuoka (JP); Hiroshi Nimura, Shizuoka (JP)

(73) Assignee: NIKKISO COMPANY LIMITED, Tokyo (JP)

( * ) Notice: Subject to any disclaimer, the term of this patent is extended or adjusted under 35 U.S.C. 154(b) by 578 days.

(21) Appl. No.: 14/505,561

(22) Filed: Oct. 3, 2014

(65) Prior Publication Data
US 2015/0021255 A1 Jan. 22, 2015

Related U.S. Application Data

(63) Continuation of application No. PCT/JP2013/060268, filed on Apr. 4, 2013.

(30) Foreign Application Priority Data

Apr. 5, 2012 (JP) .................. 2012-086526

(51) Int. Cl.
*B01D 63/00* (2006.01)
*C02F 1/44* (2006.01)
(Continued)

(52) U.S. Cl.
CPC .............. *A61J 1/1475* (2013.01); *A61M 1/14* (2013.01); *A61M 1/1619* (2014.02);
(Continued)

(58) Field of Classification Search
CPC ............ A61J 1/14; A61J 1/1475; A61M 1/14; A61M 1/16; A61M 1/168; A61M 1/1603;
(Continued)

(56) References Cited

U.S. PATENT DOCUMENTS 4,346,703 A 8/1982 Dennehey et al.
4,439,188 A 3/1984 Dennehey et al.
(Continued)

FOREIGN PATENT DOCUMENTS

JP 55-099257 A 7/1980
JP H03-73162 A 3/1991
(Continued)

OTHER PUBLICATIONS

Extended European Search Report, Application No. 13772926.5 dated Oct. 23, 2015.
(Continued)

*Primary Examiner* — Dirk Bass
*Assistant Examiner* — Hayden Brewster
(74) *Attorney, Agent, or Firm* — The Dobrusin Law Firm, P.C.

(57) ABSTRACT

A dialysate extraction device comprising a dialysate extraction means including an inlet port and an outlet port adapted to be connected to a flow path of fluid for flowing the fluid therethrough and a projected collection port for collecting the fluid flowing through the inlet and outlet port; a outer circumference wall part mounted on the dialysate extraction means so that it covers a projected end of the collection port and is projected therefrom; a connection member formed with a connection portion to be connected to the collection port and a fitting portion to be fitted into an inner circumference of the outer circumference wall part and adapted to extract the fluid through the collection port under a condition in which the connection portion is connected to the outer (Continued)

circumference wall part; and correction portions formed on the inner circumference of the outer circumference wall part for correcting position and attitude of the connection member relative to the collection port before a tip end of the connection member reaches the projected end of the collection port during insertion of the connection member into the outer circumference wall part.

20 Claims, 13 Drawing Sheets

(51) Int. Cl.
  *A61J 1/14* (2006.01)
  *A61M 1/14* (2006.01)
  *A61M 39/10* (2006.01)
  *A61M 1/36* (2006.01)
  *A61M 1/16* (2006.01)
  *F24H 1/00* (2006.01)
  *A61M 1/34* (2006.01)
(52) U.S. Cl.
  CPC ........ *A61M 1/3465* (2014.02); *A61M 1/3646* (2014.02); *A61M 1/3649* (2014.02); *A61M 39/10* (2013.01); *A61M 1/342* (2013.01)
(58) Field of Classification Search
  CPC ............. A61M 1/1605; A61M 1/1607; A61M 1/1609; A61M 1/1615; A61M 1/1619; A61M 1/1654; A61M 1/1656; A61M 1/342; A61M 1/3465; A61M 1/36; A61M 1/367; A61M 1/3609; A61M 1/3626; A61M 1/3643; A61M 1/3646; A61M 39/10; A61M 39/20; A61M 39/16; A61M 2001/165; A61M 2001/3437; A61M 2039/1088; A61M 2039/167; A61M 2202/0413; A61M 2205/12; A61M 2205/331; A61M 2205/3306; A61M 2205/75; A61M 2230/20; B01D 21/30; B01D 21/302; B01D 21/34; B01D 35/00; B01D 35/143; B01D 35/1435; B01D 35/147; B01D 35/153; B01D 61/12; B01D 61/22; B01D 61/32
  USPC .......................................................... 137/798
  See application file for complete search history.

(56) References Cited

U.S. PATENT DOCUMENTS

| | | | |
|---|---|---|---|
| 9,192,708 | B2 | 11/2015 | Iwahori et al. |
| 9,579,445 | B2 | 2/2017 | Iwahori et al. |
| 2008/0053530 | A1 | 3/2008 | Knight et al. |
| 2008/0197626 | A1* | 8/2008 | Coambs ................ A61M 39/26 285/330 |
| 2011/0172592 | A1 | 7/2011 | Lee |
| 2014/0138301 | A1 | 5/2014 | Iwahori et al. |

FOREIGN PATENT DOCUMENTS

| | | | |
|---|---|---|---|
| JP | 2003/093501 | A1 | 2/2003 |
| JP | 2004-315222 | A | 11/2004 |
| JP | 2008-539992 | A | 11/2008 |
| JP | 2009-207706 | A | 9/2009 |
| JP | 2011-161060 | A | 8/2011 |
| WO | 2006-122406 | A1 | 11/2006 |
| WO | 2009/074588 | A1 | 6/2009 |
| WO | 2013-015365 | A | 1/2013 |

OTHER PUBLICATIONS

Supplementary European Search Report dated Feb. 18, 2015 for application PCT/JP2012/068983.
Translation of International Search Report, Application No. PCT/JP2012/072976, dated Dec. 4, 2012.
European Search Report for Application No. 12830761.8 dated Apr. 10, 2015.

* cited by examiner

DIALYSATE EXTRACTION DEVICE WITH PROJECTED COLLECTION PORT, MOUNTED WALL PART AND ATTACHABLE CONNECTION MEMBER

FIELD OF THE INVENTION

The present invention relates to a dialysate extraction device comprising a dialysate extraction means adapted to be connected to a flow path of fluid and having a projected collection port for collecting the fluid flowing through the flow path.

DESCRIPTION OF BACKGROUND ART

In recent years, there has been proposed a technology for performing priming, blood-return and substitution (emergent substitution) using dialysate to be supplied to a dialyzer or a technology for using the dialysate as substitution fluid for dialysis treatment (especially on-line HDF treatment or on-line HF treatment) in a dialysis apparatus as a blood purification apparatus. In Patent Document 1 below, there is disclosed a dialysis apparatus comprising a substitution line of which one end being connected to a dialysate extraction port (collection port) arranged at a predetermined position of a dialysate introduction line and the other end being connected to a blood circuit (arterial blood circuit and venous blood circuit), and a substitution pump arranged on the substitution line. In such a dialysis apparatus, the dialysate in the dialysate introduction line can be supplied to the blood circuit (arterial blood circuit and venous blood circuit) by driving the substitution pump.

In usual, a cap (open/close member) are detachably mounted on the dialysate extraction port, and thus the substitution line can be connected to the dialysate extraction port when the cap is removed and leakage of the dialysate flowing through the dialysate introduction line can be prevented by mounting the cap on the dialysate extraction port when the substitution line is not connected thereto. For example, when performing cleaning or disinfection of pipes such as the dialysate introduction line and dialysate discharging line through which dialysate flows, leakage of flushing water or disinfection liquid can be prevented by flowing flushing water or disinfection liquid through pipes with keeping the cap mounted on the collection port.

On the other hand, a connection member is mounted on a tip end of a connection line such as the substitution line adapted to be connected to the collection port to extract dialysate flowing through the dialysate introduction line by connecting the connection member to the collection port and then to supply the extracted dialysate to a desired portion (e.g. blood circuit etc.) via the connection line. In addition, it is possible to extract a predetermined amount of dialysate flowing through the dialysate introduction line by connecting the tip end of the connection member comprising a syringe etc.

DOCUMENT OF PRIOR ART

Patent Document

Patent Document 1: JP 2004-313522 A

DISCLOSURE OF THE INVENTION

Problems to be Solved by the Invention

However, in the dialysate extraction device of the prior art described above, it is afraid that a near part of the connection portion of the connection member would be come in contact with a non-cleaned part of a outer circumference wall part of the dialysate extraction device by a medical worker although the collection port is sufficiently cleaned or disinfected. Under such situation, it is afraid that the contaminated part of the connection portion of the connection member would come in contact with the collection port and thus the cleanliness of the collection port would be impaired if the position or attitude of the connection member relative to the collection port is deviated each other during connection of the connection member to the collection port.

It is, therefore, an object of the present invention to provide a dialysate extraction device which can surely keep the cleanliness of the collection port during connection of the connection member to the collection port.

Means for Solving the Problems

For achieving the object of the present invention, there is provided according to the present invention and the teachings herein provide a dialysate extraction device comprising a dialysate extraction means including an inlet port and an outlet port adapted to be connected to a flow path of fluid for flowing the fluid therethrough and a projected collection port for collecting the fluid flowing through the inlet and outlet port; a outer circumference wall part mounted on the dialysate extraction means so that it covers a projected end of the collection port and is projected therefrom; a connection member formed with a connection portion to be connected to the collection port and a fitting portion to be fitted into an inner circumference of the outer circumference wall part and adapted to extract the fluid through the collection port under a condition in which the connection portion is connected to the outer circumference wall part; and correction portions formed on the inner circumference of the outer circumference wall part for correcting position and attitude of the connection member relative to the collection port before a tip end of the connection member reaches the projected end of the collection port during insertion of the connection member into the outer circumference wall part.

According to the present invention as taught herein, there is provided a dialysate extraction device of the teachings herein wherein a length between the projected end of the collection port and a tip end of the outer circumference wall part is substantially same as or larger than a length between the tip end of the connection member and the fitting portion of the connection member.

According to the present invention as taught herein, there is provided a dialysate extraction device of the teachings herein wherein the correction portions are formed as tapered portions formed on the inner circumference of the outer circumference wall part.

According to the present invention as taught herein, there is provided a dialysate extraction device of the teachings herein wherein the fitting portion of the connection member comprises a seal member for sealing between the outer circumference of the connection member and the inner circumference of the outer circumference wall part.

According to the present invention as taught herein, there is provided a dialysate extraction device of the teachings herein wherein the dialysis extraction device further comprises an open/close member detachably mounted on the collection port for opening and closing the collection port, and wherein the collection port forms a guide path for guiding the fluid introduced through the inlet port toward the projected end of the collection port and a discharge path for discharging the fluid guided by the guide path toward the outlet port under a condition in which the open/close member is mounted on the outer circumference wall part.

According to the present invention as taught herein, there is provided a dialysate extraction device of the teachings herein wherein the open/close member is provided with a seal member for sealing between the outer circumference or the tip end face of the outer circumference wall part and the open/close member.

According to the present invention as taught herein, there is provided a blood purification apparatus comprising the dialysate extraction device of any one of the teachings herein.

According to the present invention as taught herein, there is provided a connection line having a tip end to which the connection member of any one of the teachings herein is connected.

Effects of the Invention

According to the present inventions as taught herein, since correction portions are formed on the inner circumference of the outer circumference wall part for correcting position and attitude of the connection member relative to the collection port before a tip end of the connection member reaches the projected end of the collection port during insertion of the connection member into the outer circumference wall part, it is possible to surely keep the cleanliness of the collection port during connection of the connection member to the collection port.

According to the present inventions as taught herein, since a length between the projected end of the collection port and a tip end of the outer circumference wall part is substantially same as or larger than a length between the tip end of the connection member and the fitting portion of the connection member, it is possible to correct position and attitude of the connection member relative to the collection port before a tip end of the connection member reaches the projected end of the collection port and thus to surely keep the cleanliness of the collection port during connection of the connection member to the collection port.

According to the present inventions as taught herein, since the correction portions are formed as tapered portions formed on the inner circumference of the outer circumference wall part, it is possible to smoothly and surely correct position and attitude of the connection member relative to the collection port before a tip end of the connection member reaches the projected end of the collection port.

According to the present invention as taught herein, since the fitting portion of the connection member comprises a seal member, leak of fluid can be effectively prevented even if connection of the connection member relative to the collection port is not correctly performed.

According to the present invention as taught herein, since the collection port forms a guide path for guiding the fluid introduced through the inlet port toward the projected end of the collection port and a discharge path for discharging the fluid guided by the guide path toward the outlet port under a condition in which the open/close member is mounted on the outer circumference wall part, it is possible to flow flushing water or disinfection liquid through the guide path and discharge path and to surely perform flushing and disinfection of the inside of the collection port. In addition, since the collection port has both the functions of collection of fluid and of definition of the guide path and discharge path, simplification of structure can be attained with eliminating any other definition means.

According to the present invention as taught herein, since the open/close member is provided with a seal member for sealing between the outer circumference or the tip end face of the outer circumference wall part and the open/close member, it is possible to more surely define the guide path and the discharge path under a condition in which the open/close member is mounted on the collection port and thus to more effectively perform flow of the flushing water and disinfection liquid.

According to the present invention as taught herein, it is possible to provide a blood purification apparatus which can keep cleanliness of the collection port during connection of the connection member to the collection port.

According to the present invention as taught herein, it is possible to provide a connection line which can keep cleanliness of the collection port during connection of the connection member to the collection port.

ONE PREFERABLE MODE FOR CARRYING OUT THE INVENTION

Preferable embodiments of the present invention will be hereinafter described with reference to the drawings.

Figure 1:
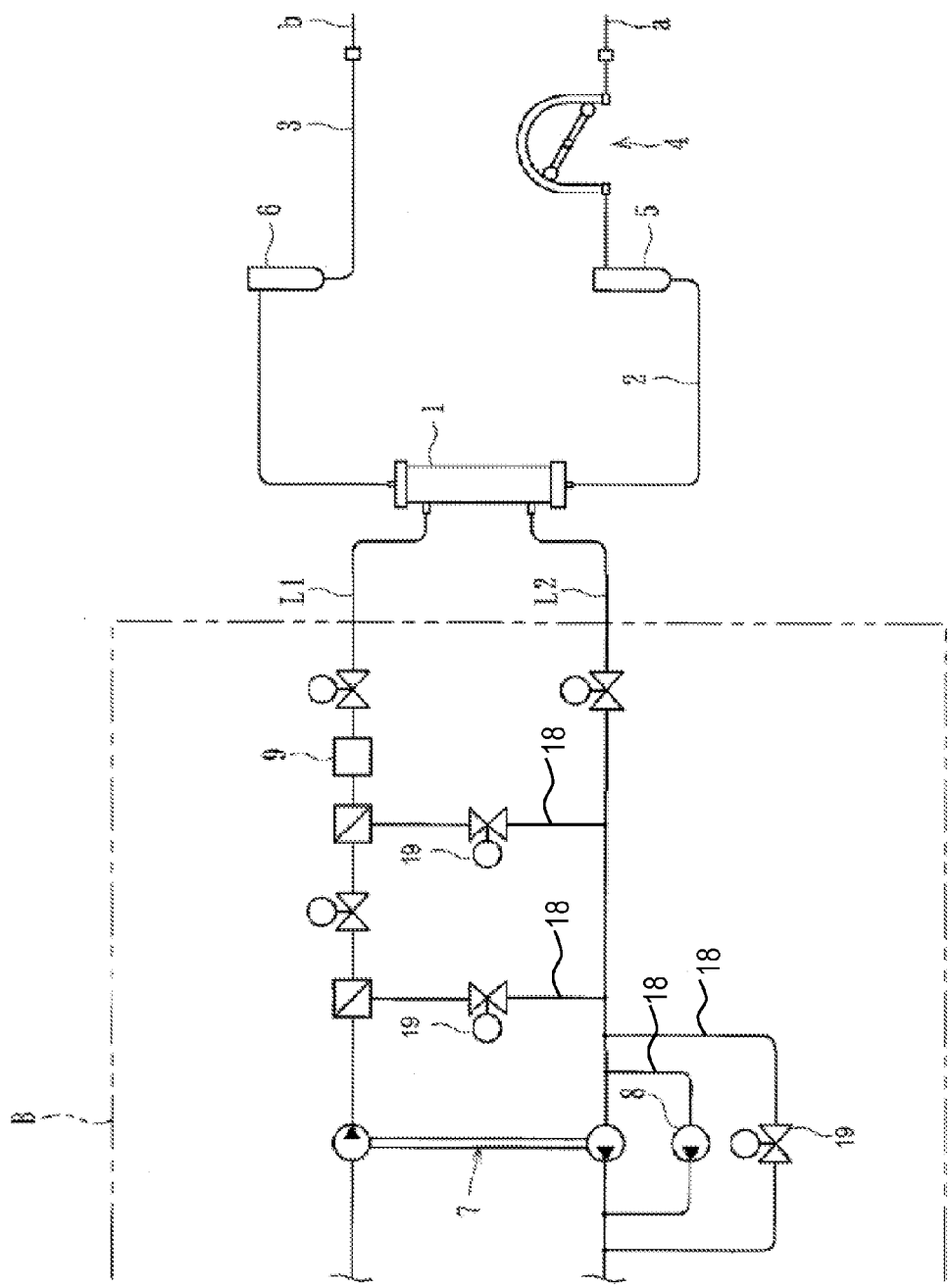
FIG. 1 A general schematic view showing a blood purification apparatus to which a dialysate extraction device of the present invention is applied.

The dialysate extraction device of the present invention can be applied to a blood purification apparatus used in blood purification treatment (hemodialysis treatment) and adapted to be used to collect dialysate. As shown in FIG. 1, the blood purification apparatus to which the dialysate extraction device of the present invention is applied mainly comprises a blood circuit in which an arterial blood circuit 2 and a venous blood circuit 3 are connected to a dialyzer 1 (blood purification instrument) and a main body B of dialysis apparatus provided with a dialysate introduction line L1 and a dialysate discharge line L2.

The dialyzer 1 for purifying blood is connected to the arterial blood circuit 2, venous blood circuit 3, the dialysate introduction line L1 and the dialysate discharge line L2 and intended to extracorporeally circulate blood of a patient collected via an arterial puncture needle "a" through the blood circuit and return blood to a body of patient via a venous puncture needle "b" after treatments of blood purification and ultrafiltration in the dialyzer 1. Reference numerals 5, 6 denote air trap chambers.

A duplex pump 7 is connected to the dialysate introduction line L1 and the dialysate discharging line L2 for supplying dialysate prepared as having predetermined concentration to the dialyzer 1 and discharging it therefrom. In addition, a plurality of bypass lines 18 and electromagnetic valves 19 are arranged on arbitrary positions in the main body B of dialysis apparatus and an ultrafiltration pump 8 is connected to a bypass line for bypassing the duplex pump 7.

The disinfection or washing can be performed by introducing disinfection liquid (hot water or liquid disinfection chemicals) or washing water (purified water) from the outside (e.g. dialysate supplying apparatus) of the main body B of dialysis apparatus and by substituting with liquid (dialysate etc.) in pipes in the main body B of dialysis apparatus after removing the tip ends of the dialysate introduction line L1 and the dialysate discharge line L2 from the dialyzer 1 and connecting the tip ends each other e.g. by using a coupler to disconnect pipes. In this case, it may be possible to perform the substitution by dividing a flow path from the dialysate discharge line L2, leading the tip end of the divided flow path into a tank containing disinfection liquid etc. and introducing the disinfection liquid etc. in the tank to the pipe.

The dialysate extraction device of a first embodiment of the present invention shown in FIGS. 2~10 is connected to the dialysate introduction line L1. The dialysate extraction device comprises a dialysate extraction means 9 including an inlet port 9a and an outlet port 9b adapted to be connected to a flow path L1 of fluid for flowing the fluid therethrough and a projected collection port 12 for collecting the fluid flowing through the inlet and outlet port 9a, 9b; a cap (open/close member) 10 detachably mounted on the collection port 12 of the dialysate extraction means 9 for opening and closing the collection port 12; a outer circumference wall part 13 mounted on the dialysate extraction means 9 so that it covers a projected end 12a of the collection port 12 and is projected therefrom; and a connection member 15 adapted to be connected to the collection port 12 when the cap 10 is removed from the collection port 12.

More particularly, the dialysate introduction line L1 is connected to both an inlet port 9a and an outlet port 9b of the dialysate extraction means 9 so that dialysate can flow through the dialysate extraction means 9. The flow path through which dialysate flows from the inlet port 9a to the outlet port 9b is formed as a L-shaped passage turned substantially 90° at a divisional portion P and the collection port 12 is arranged on a substantially same straight line with respect to the inlet port 9a.

Figure 2:
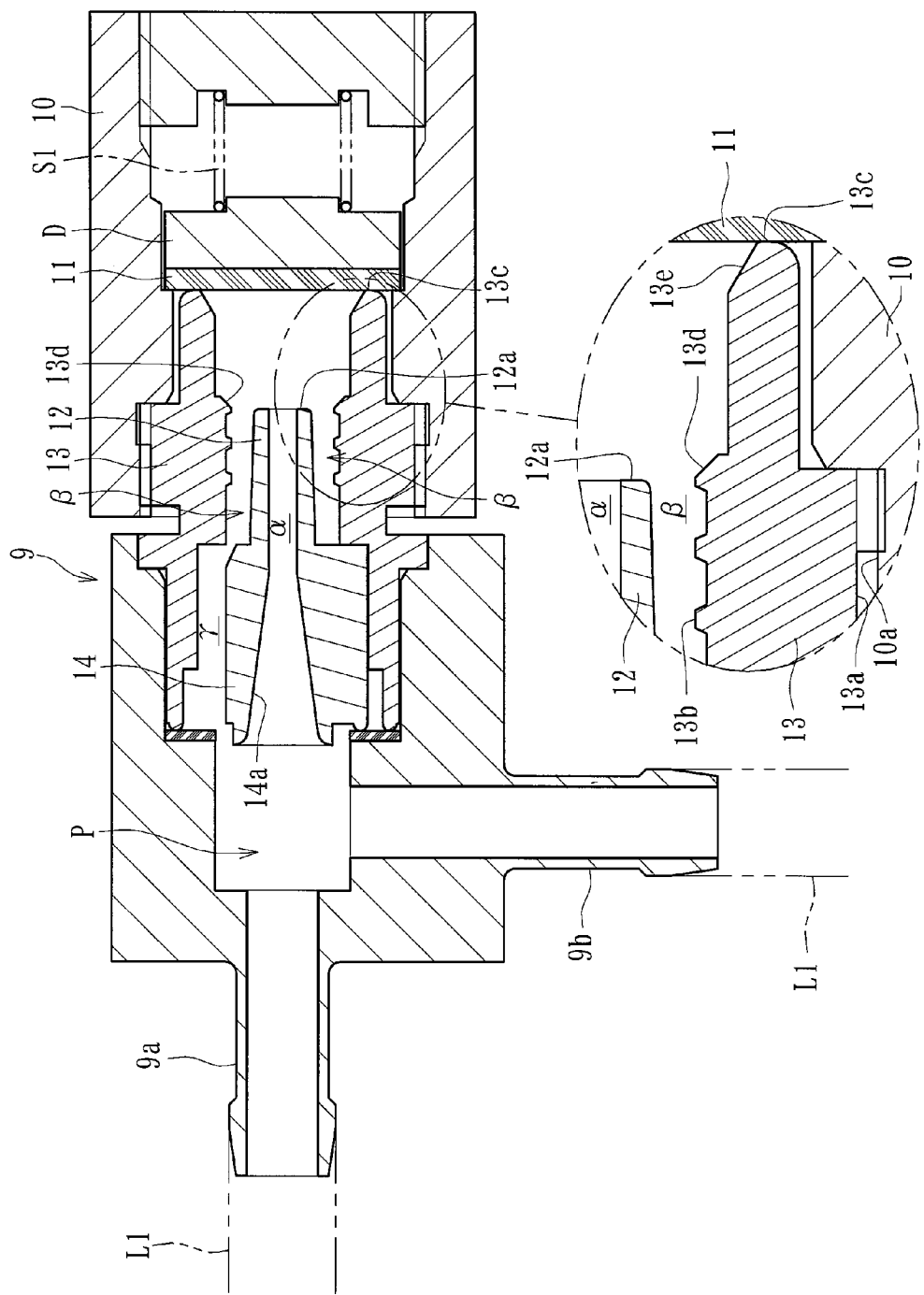
FIG. 2 A longitudinal section view of a dialysate extraction device of a first embodiment of the present invention showing a state in which an open/close member (cap) is mounted on a collection port.

The outer circumference wall part 13 covers around an outer circumference of the collection port 12 and is formed on the outer circumference with a male thread 13a engageable with a female thread 10a of the cap (open/close member) 10 and on the inner circumference with a female thread 13b (see FIG. 2). A clearance of predetermined dimension is formed between the inner circumference of the outer circumference wall part 13 and the outer circumference of the collection port 12 to form a discharge path β later mentioned.

The outer circumference wall part 13 is formed so that it is projected from a projected end 12a of the collection port 12 to cover the collection port 12 around it. That is, since the projected dimension (projected length) of the outer circumference wall part 13 is larger than that of the collection port 12, the projected end 12a can be covered by the outer circumference wall part 13. Accordingly, it is possible to prevent the collection port 12 from being touched by fingers of a medical worker and thus to surely improve health supervision even if the cap 10 is removed from the collection port 12.

Figure 3:
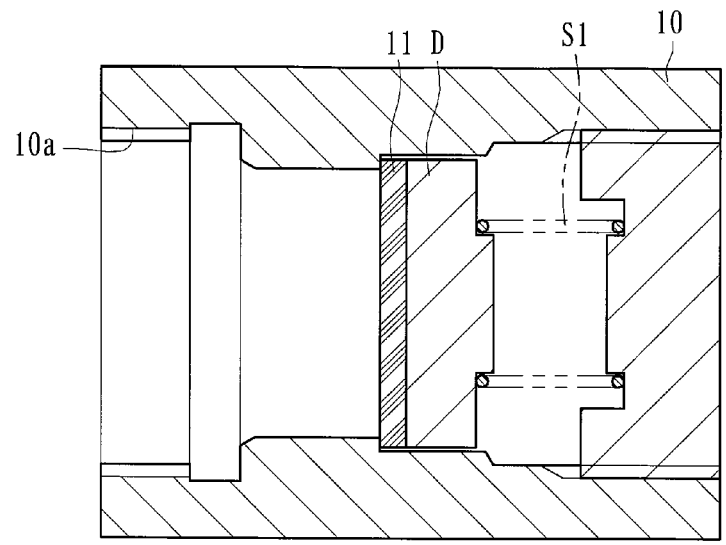
FIG. 3 A longitudinal section view showing the cap (open/close member) of the dialysate extraction device.
Figure 4:
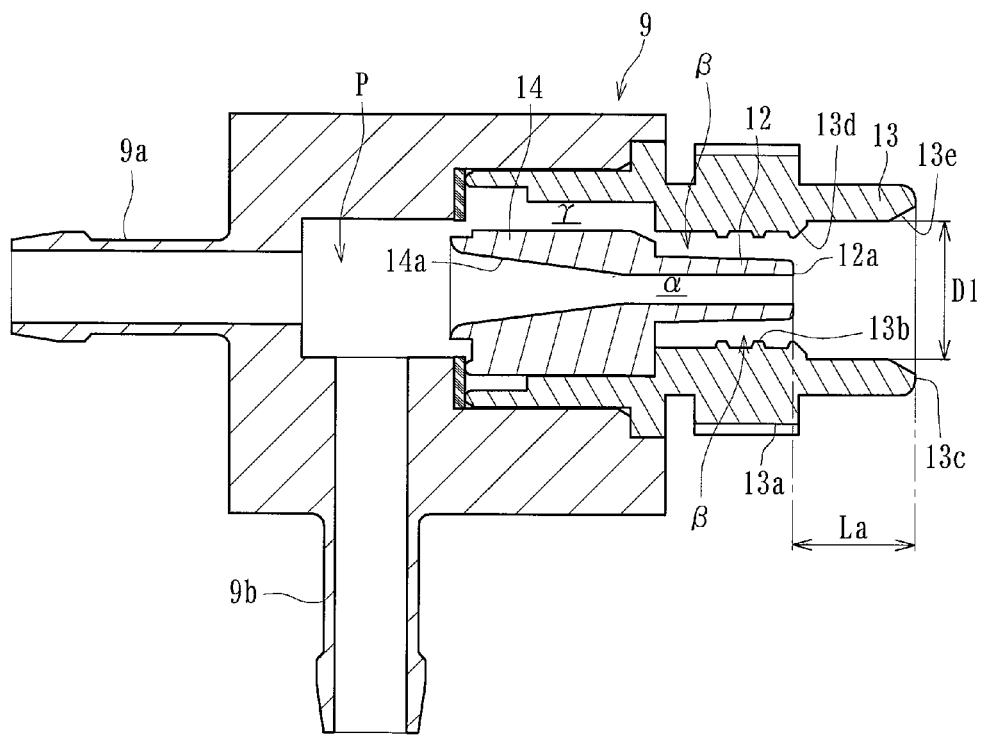
FIG. 4 A longitudinal section view of a dialysate extraction means of a dialysate extraction device showing a state in which the open/close member (cap) is removed from the collection port.

The cap (open/close member) 10 can be mounted on the outer circumference wall part 13 by engaging the female thread 10a with the male thread 13a of the outer circumference wall part 13. As shown in FIG. 3, the cap 10 is provided with a seal member 11 for sealing contacting surfaces between the tip end 13c of the outer circumference wall part 13 and the cap 10. The seal member 11 is mounted on one surface of a mount member D and normally urged toward the tip end 13c (i.e. toward the collection port 12) together with the mount member D by a spring S1 to attain sure seal between the outer circumference wall part 13 and the cap 10. Although it is described that the seal member 11 can seal contacting surfaces between the tip end 13c of the outer circumference wall part 13 and the cap 10, it is possible to replace with or add to the seal member 11 which can seal the outer circumference of the outer circumference wall part 13 and the cap 10.

The collection port 12 forms a guide path α for guiding the fluid introduced through the inlet port 9a toward the projected end 12a of the collection port 12 and a discharge path β for discharging the fluid guided by the guide path α toward the outlet port 9b under a condition in which the open/close member 10 is mounted on the outer circumference wall part 13. That is, when the cap (open/close member) 10 is mounted on the outer circumference wall part 13, the tip end 13c of the outer circumference wall part 13 is sealed and a sealed space is formed within the outer circumference wall part 13 and the sealed space is divided to the guide path α inside the collection port 12 and the discharge path β between the outer circumference of the collection port 12 and the inner circumference of the outer circumference wall part 13.

As described above, the collection port 12 has a function for the connection member 15 (FIG. 5) to be connected thereto to extract fluid from the collection port 12 and a function for defining the guide path α and the discharge path β. Although the collection port 12 is shown as having a circular cross-section, any other cross-sectional configuration (e.g. rectangular cross-section) may be used as long as it is able to define both the guide path α and the discharge path β.

The dialysate extraction means 9 is formed with a connection path γ for connecting the discharge path β and a path in the divisional portion P. Accordingly, fluid introduced toward the tip end 12a of the collection port 12 through the divisional portion P and the guide path α from the inlet port 9a can be discharged from the outlet port 9b through the discharge path β and the connection path γ with joining fluid flowing toward the outlet port 9b through the divisional portion P from the inlet port 9a.

A pressure-difference generation part 14 for increasing a pressure of fluid flowing toward the guide path α higher than that of fluid flowing toward the outlet port 9b is integrally formed with the collection port 12. The pressure-difference generation part 14 is arranged near the divisional portion P and has a flow path 14a for fluid flowing from the inlet port 9a to the tip end 12a of the collection port 12. The flow path 14a is formed by a tapered surface of which diameter is gradually reducing toward the tip end 12a (toward a right direction in FIG. 2). Accordingly, it is possible to increase a pressure of fluid flowing from the inlet port 9a to the extraction member 12 higher relative to that of fluid flowing from the inlet port 9a to the outlet port 9b.

Since the pressure-difference generation part 14 is integrally formed with the collection port 12, it is possible to reduce the number of parts of the dialysate extraction device and thus to reduce manufacturing cost and maintenance cost of the dialysate extraction device. It is of course to separately manufacture the pressure-difference generation part 14 and the collection port 12 and combine them as an integral part.

Figure 5:
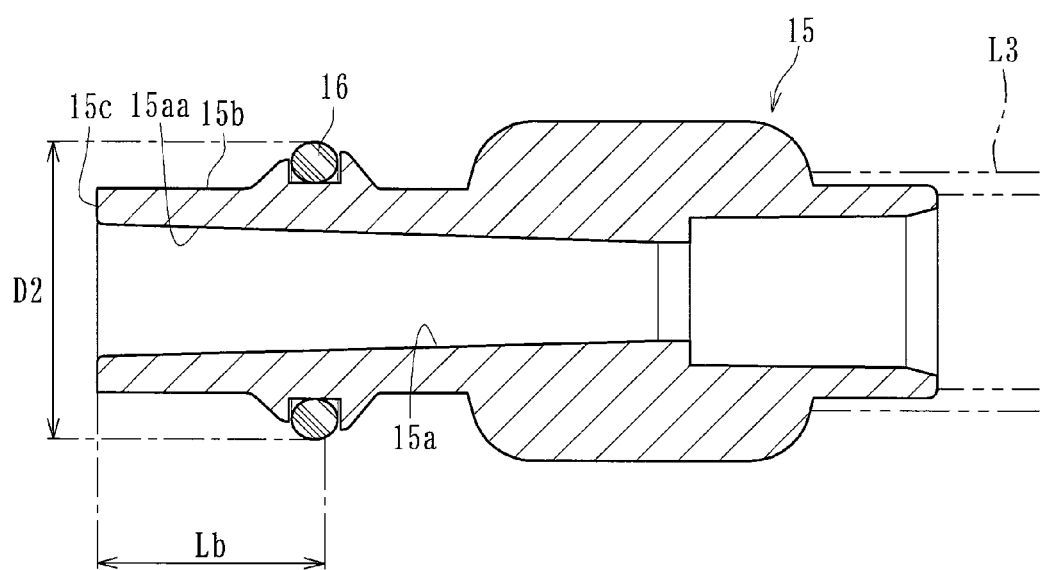
FIG. 5 A longitudinal section view of connection member adapted to be connected to the collection port of the dialysate extraction device.

As shown in FIG. 5, the connection member 15 is adapted to be connected to a connection line L3 for flowing fluid extracted from the collection port 12 therethrough and formed of a substantially outer circumference wall part having an inner circumference 15a and an outer circumference 15b. The inner circumference 15a of a tip end 15c (tip end of left-side of FIG. 5) of the connection member 15 forms a connection portion 15aa into which the tip end 12a of the collection port 12.

A fitting portion 16 (e.g. O-ring) as a seal member is arranged on the outer circumference 15b of the connection member 15 for being fit into the inner circumference of the outer circumference wall part 13. The fitting portion 16 is contacted with the inner circumference of the outer circumference wall part 13 and seals the contacted surface between the outer circumference 15b of the connection member 15 and the inner circumference of the outer circumference wall part 13 when the connection member 15 is connected to the collection port 12. That is, an outer diameter D2 (FIG. 5) of the fitting portion 16 is same as or slightly larger an inner diameter D1 (FIG. 4) of the outer circumference wall part 13 and exhibits good sealing function when the connection member 15 is fitted into the outer circumference wall part 13.

Thus, the connection line L3 can be connected to the collection port 12 by inserting the connection member 15 into the outer circumference wall part 13 and by engaging the fitting portion (seal member) 16 with the inner circumference of the outer circumference wall part 13. Any other portion engageable with the inner circumference of the outer circumference wall part 13 may be formed on the outer circumference 15b of the connection member 15 in place of the fitting portion 16. Also in this case, the outer diameter D2 of the connection member 15 is set substantially same as (strictly, slightly larger than) the inner diameter D1 of the outer circumference wall part 13.

The connection line L3 can be connected, for example, to the air trap chamber 5 connected to the arterial blood circuit 2 or to the air trap chamber 6 connected to the venous blood circuit 3 to supply dialysate in the dialysate introduction line L1 to the arterial blood circuit 2 or to the venous blood circuit 3. Accordingly, it is possible to perform priming, blood-return and substitution using dialysate, or to use the dialysate as substitution fluid for on-line HDF treatment or on-line HF treatment.

As described above, since the region from the tip end 15c to inside of the inner circumference 15a of the connection member 15 is inserted onto the outer circumference of the collection port 12 and accordingly the connection portion 15aa of the connection member 15 to the collection port 12 corresponds to the inner circumference 15a (inside surface of the connection member 15), it is possible to prevent the connection portion 15aa from being contacted by fingers of medical workers and thus to more surely improve health supervision.

According to the dialysate extraction device of the present invention, correction portions (tapered portions 13d, 13e) are formed on the inner circumference of the outer circumference wall part 13 for correcting position (radial position) and attitude (inclination) of the connection member 15 relative to the collection port 12 before a tip end 15c of the connection member 15 reaches the projected end 12a of the collection port 12 during insertion process (connection process) of the connection member 15 into the outer circumference wall part 13.

The correction portion comprises the tapered portion 13d formed on the inner circumference of the outer circumference wall part 13 at a position outer side (right side in FIG. 2) of the projected end 12a of the collection port 12 and the tapered portion 13e formed on an opening edge of the outer circumference wall part 13. These tapered portions 13d, 13e are adapted to be abutted respectively by the tip end 15c and the fitting portion 16 of the connection member 15 during the inserting process (connection process) of the connection member 15 to the outer circumference wall part 13 (i.e. to the collection port 12).

Figure 7:
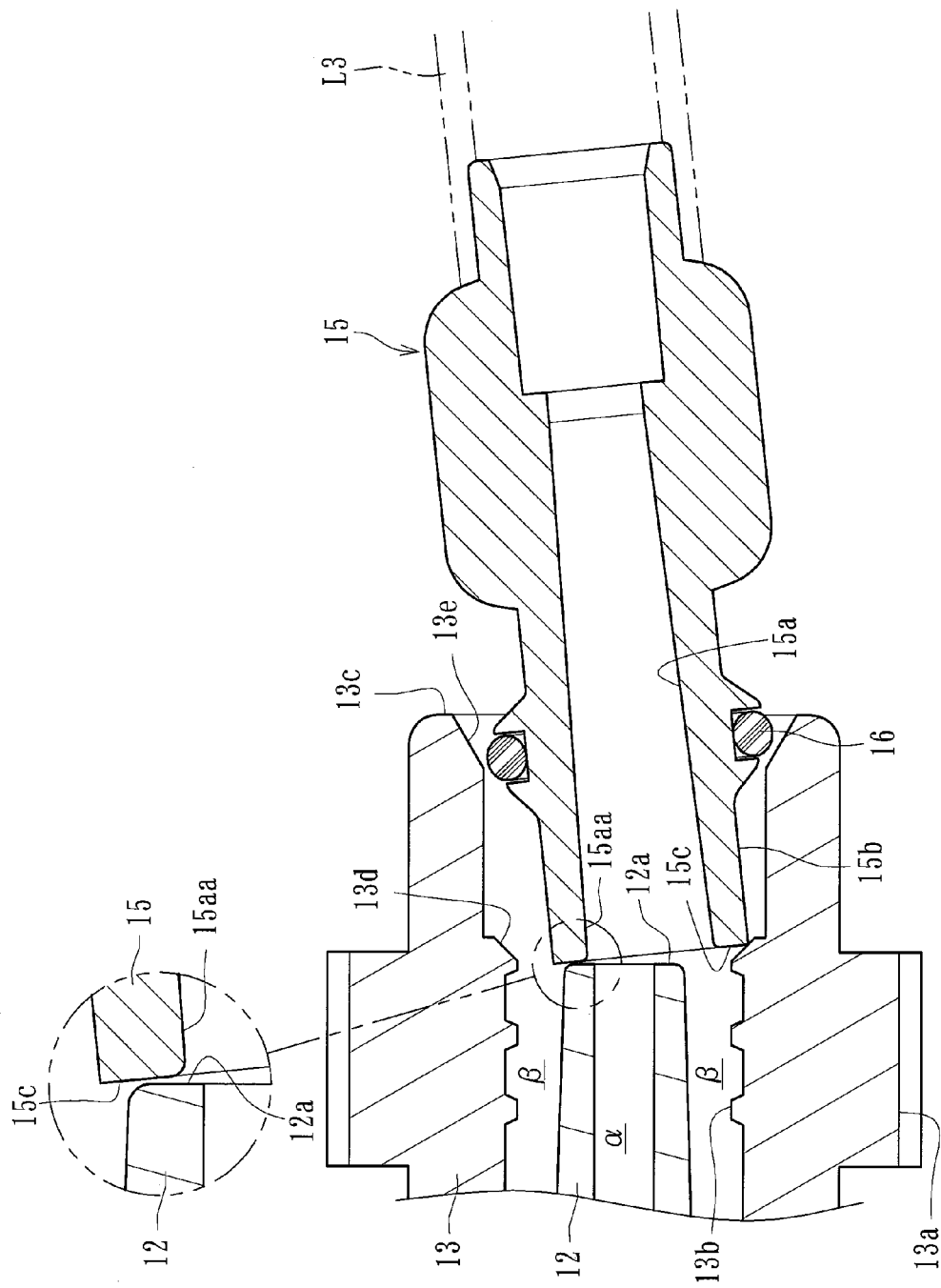
FIG. 7 A longitudinal section view of showing a process in which the connection member is connected to the collection port of the dialysate extraction device prior to correction of position and attitude of the connection member relative to the collection port.
Figure 8:
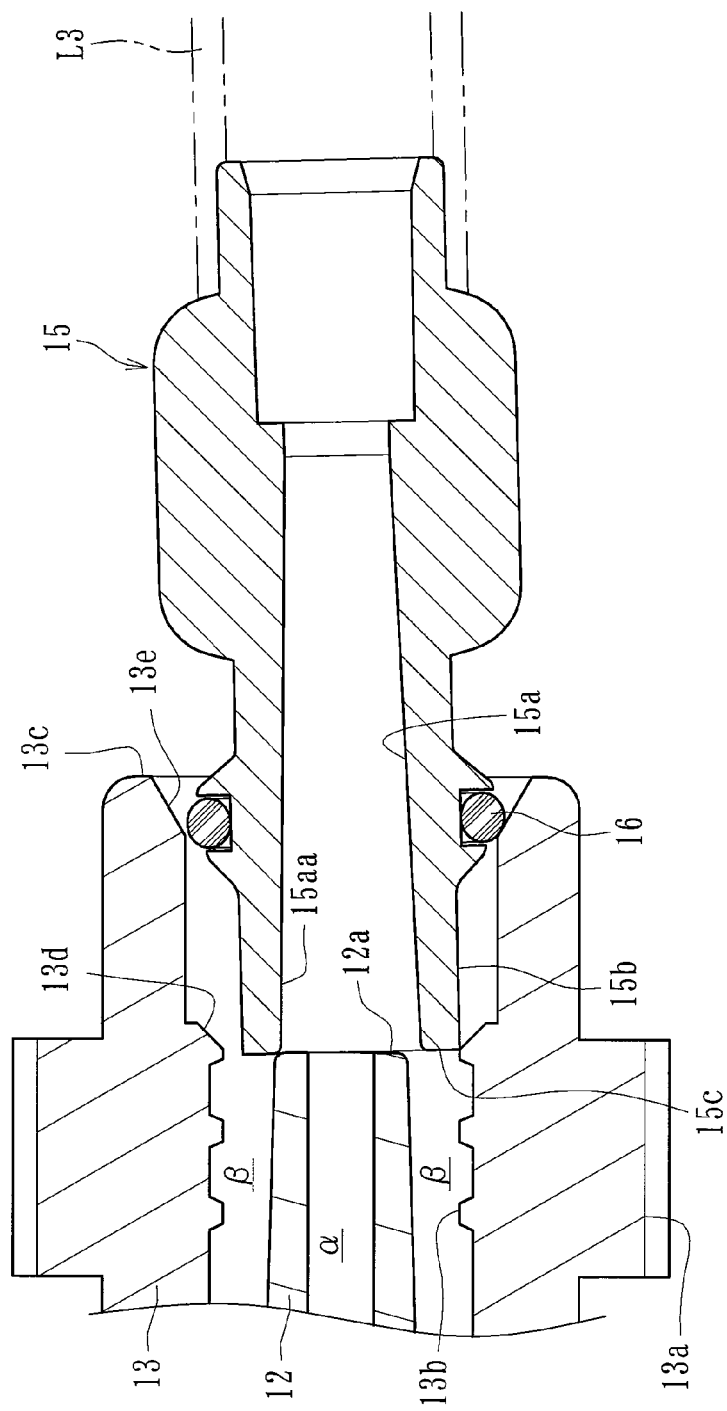
FIG. 8 A longitudinal section view of showing a process in which the connection member is connected to the collection port of the dialysate extraction device after correction of position and attitude of the connection member relative to the collection port.

If the position or attitude of the connection member 15 relative to the collection port 12 is deviated each other during connection of the connection member 15 to the outer circumference wall part 13, the tip end 15c of the connection member 15 will be abutted against the tapered portion 13d (see FIG. 7) and the fitting portion 16 will be abutted against the tapered portion 13e (see FIG. 8). Accordingly, the deviation of the position or attitude of the connection member 15 relative to the collection port 12 can be corrected. On the other hand, if the position or attitude of the connection member 15 relative to the collection port 12 is not deviated each other, no abutment against the tapered portions 13d, 13e is caused.

In addition, according to the dialysate extraction device of the present invention, a length La (FIG. 4) between the projected end 12a of the collection port 12 and a tip end 13c of the outer circumference wall part 13 is substantially same as or larger than a length Lb (FIG. 5) between the tip end 15c of the connection member 15 and the fitting portion 16 (max. diameter portion) of the connection member 15 (i.e. La≥Lb). This makes it possible to commence the fitting of the fitting portion (seal member) 16 before the tip end 15c of the connection member 15 reaches the projected end 12a of the collection port 12 during connection of the connection member 15 to the collection port (or the outer circumference wall part 13).

Figure 6:
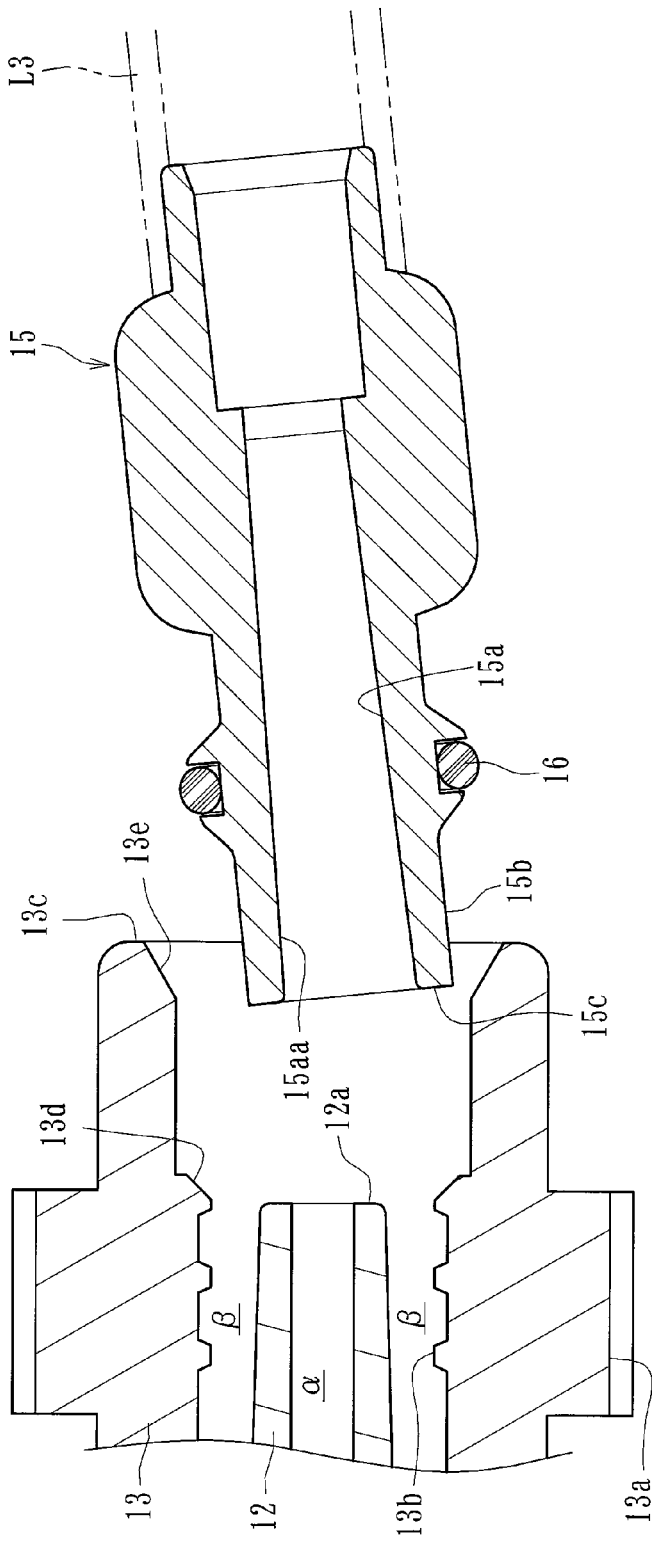
FIG. 6 A longitudinal section view of showing a process in which the connection member is connected to the collection port of the dialysate extraction device when the connection member is inserted into a outer circumference wall part of the dialysate extraction device.

Then, action of the correction portions of the outer circumference wall part 13 of the present invention during inserting process (connection process) of the connection member 15 to the outer circumference wall part 13 will be described more in detail with respect to FIGS. 6~10. Supposing that the position and attitude of the connection member 15 is deviated relative to the collection port 12 during insertion of the tip end 15c of the connection member 15 into the outer circumference wall part 13 as shown in FIG. 6, the tip end 15c of the connection member 15 will be abutted against the tapered portion 13d of the outer circumference wall part 13 before the tip end 15c of the connection member 15 reaches the projected end 12a of the collection port 12 as shown in FIG. 7.

With further proceeding insertion of the connection member 15, the attitude of the outer circumference wall part 15 will be changed by the gradient of tapered portion 13d as shown in FIG. 8. Accordingly, whole the connection member 15 is moved to a direction in which a direction of the opening of the collection port 12 and a direction of the opening of the connection member 15 corresponds to each other and thus the attitude of the connection member 15 can be corrected. In this case, if the correction of the connection member 15 is insufficient, the fitting portion 16 is abutted against the tapered portion 13e.

With further proceeding insertion of the connection member 15, the radial deviation of the outer circumference wall part 15 relative to the collection port 12 will be corrected by the gradient of tapered portions 13d, 13e. That is, the connection member 15 can be corrected and occupy a regular state by the tapered portions 13d, 13e forming the correction portion during inserting process of the outer circumference wall part 15 so that the connection member 15 is centered relative to the collection port 12.

Figure 9:
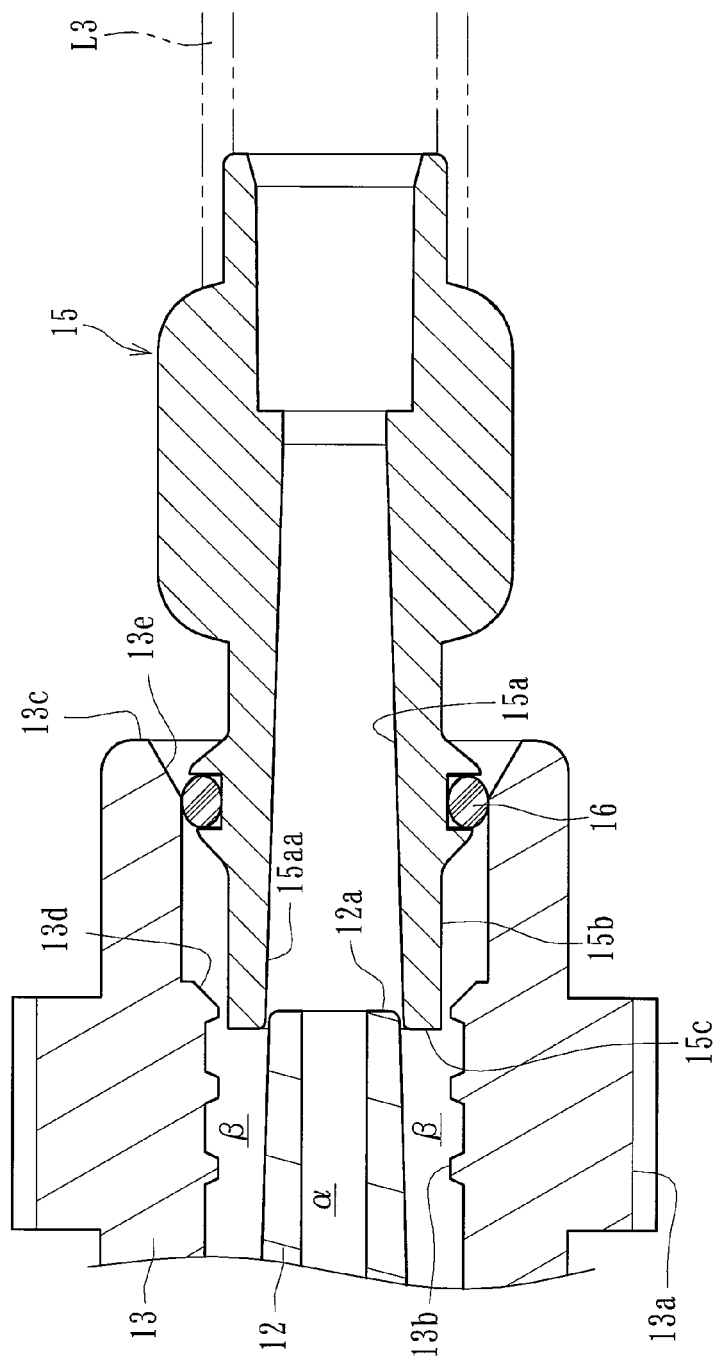
FIG. 9 A longitudinal section view of showing a process in which the connection member is connected to the collection port of the dialysate extraction device after correction of position and attitude of the connection member relative to the collection port and in the middle of connection of the connection member to the collection port.
Figure 10:
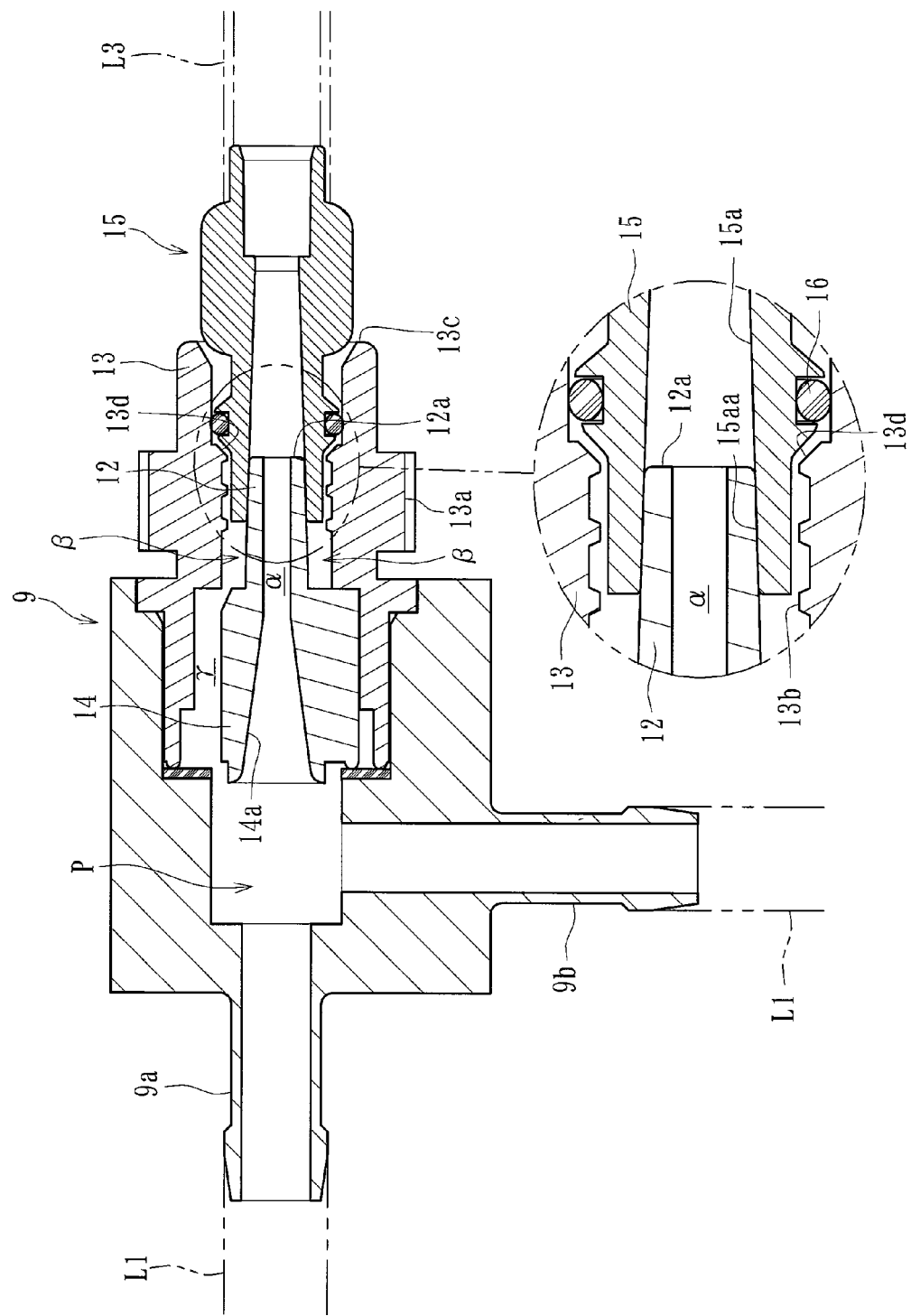
FIG. 10 A longitudinal section view of showing a state in which the connection member has been connected to the collection port of the dialysate extraction device.

Then further continuing insertion of the connection member 15 into the outer circumference wall part 13 with keeping the corrected condition of the connection member 15, an area near the tip end 15c of the connection member 15 will commence to slide on the outer circumference the collection port 12 (FIG. 9). The connection of the connection member 15 to the collection port 12 can be completed by further sliding the connection member 15 on the collection port 12 by a predetermined distance and thus the connection portion 15aa of the connection member 15 is closely contacted with the outer circumference of the collection port 12 (FIG. 10). Accordingly, it is possible to prevent the tip end 15c of the connection member 15 from being contacted with the collection port 12 if the end face of the tip end 15c of the connection member 15 would be contacted with a non-cleaned part (e.g. outer circumference surface of the outer circumference wall part 13).

Figure 11:
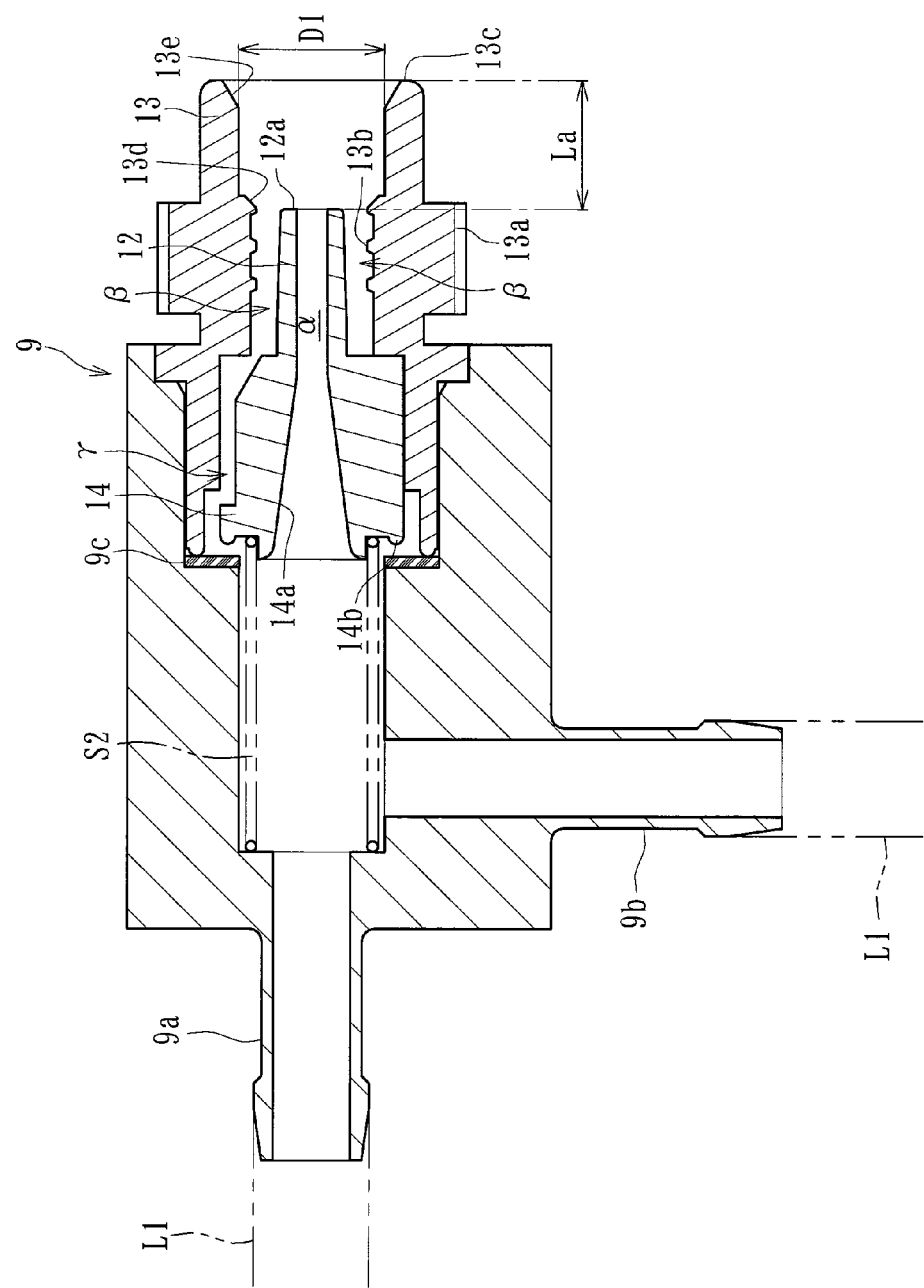
FIG. 11 A longitudinal section view of a dialysate extraction device of a second embodiment of the present invention showing a state in which the open/close member (cap) is removed from the collection port.
Figure 12:
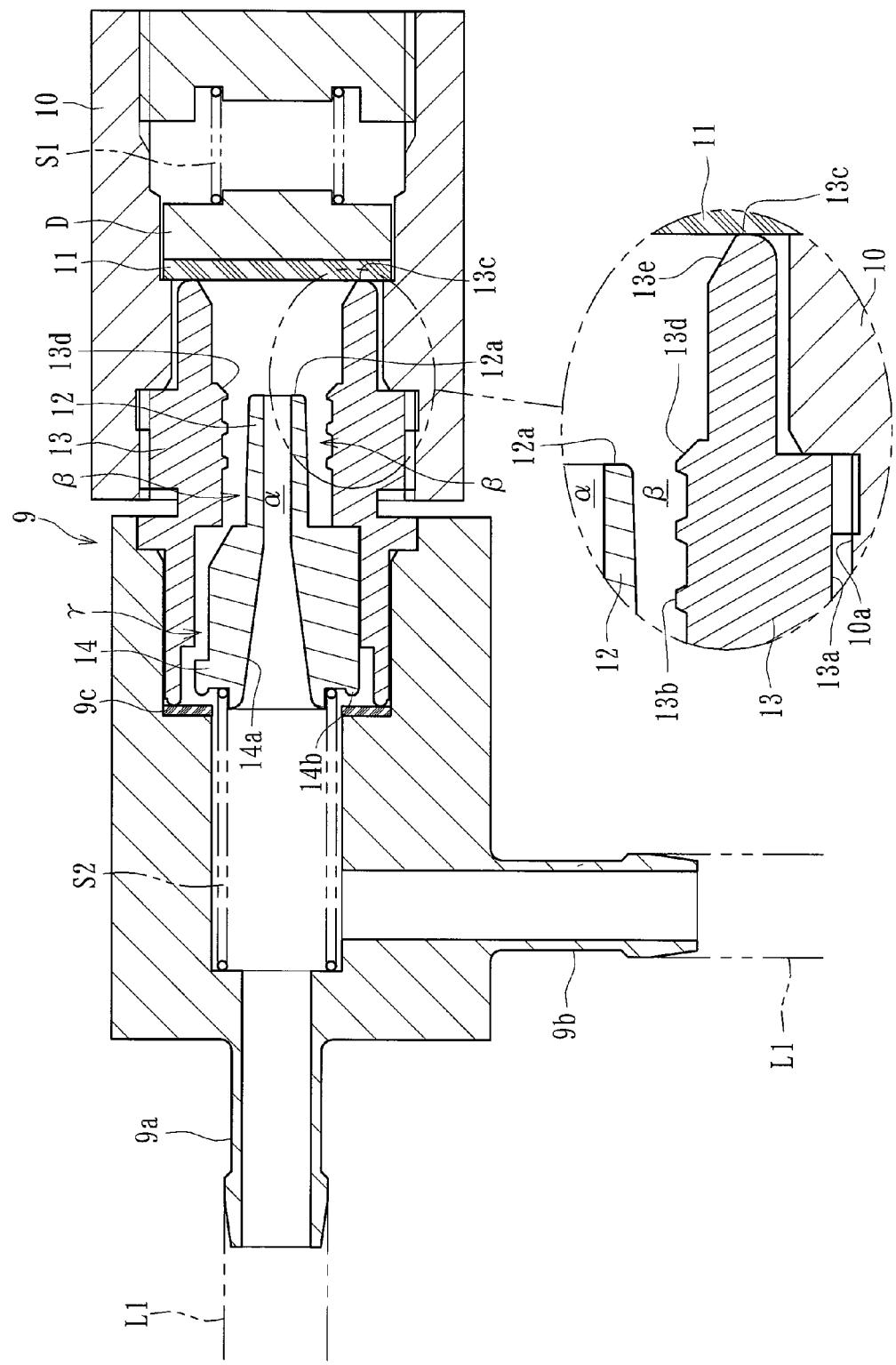
FIG. 12 A longitudinal section view of a dialysate extraction device of a second embodiment of the present invention showing a state in which the open/close member (cap) is mounted on the outer circumference wall part.
Figure 13:
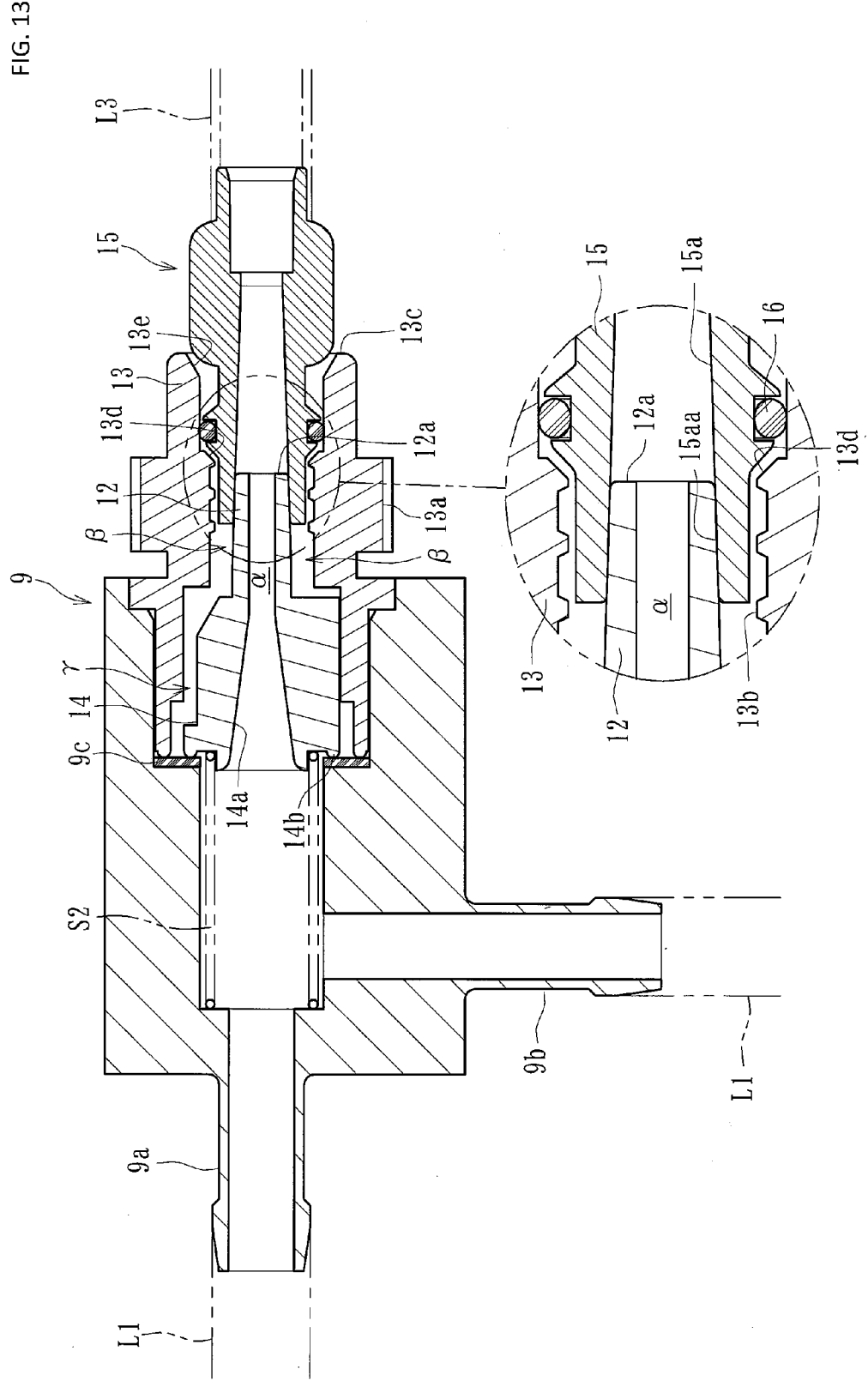
FIG. 13 A longitudinal section view of a dialysate extraction device of a second embodiment of the present invention showing a state in which the connection member is mounted on the collection port.

Then, a dialysate extraction device of a second embodiment of the present invention will be described. Similarly to the first embodiment, the dialysate extraction device of the second embodiment comprises, as shown in FIGS. 11~13, a dialysate extraction means 9 including an inlet port 9a and an outlet port 9b adapted to be connected to a flow path L1 of fluid for flowing the fluid therethrough and a projected collection port 12 for collecting the fluid flowing through the inlet and outlet port 9a, 9b; a cap (open/close member) 10 detachably mounted on the collection port 12 of the dialysate extraction means 9 for opening and closing the collection port 12; a outer circumference wall part 13 mounted on the dialysate extraction means 9 so that it covers a projected end 12a of the collection port 12 and is projected therefrom; and a connection member 15 adapted to be connected to the collection port 12 when the cap 10 is removed from the collection port 12. Same reference numerals as those used for designating structural elements of the first embodiment are also used for designating structural elements of the second embodiment and detailed description of them will be omitted.

Similarly to the first embodiment, the pressure-difference generation part 14 and the collection port 12 are formed as an integral part (e.g. integrally molded part), however, it is different from the first embodiment in that it is movable within the dialysate extraction means 9. In addition, the pressure-difference generation part 14 is formed with a sealed portion 14b to be sealed by a seal member 9c and the integrally formed pressure-difference generation part 14 and the collection port 12 are normally urged by a spring S2 toward a direction in which the sealed portion 14b is separated from the seal member 9c.

During the connection process of the connection member 15 to the collection port 12 (i.e. insert process of the connection member 15 to the outer circumference wall part 13), the pressure-difference generation part 14 and the collection port 12 are moved against the urging force of the spring S2 and the sealed portion 14b is abutted against the seal member 9c to close the connection path γ.

Accordingly, outflow of fluid through the discharge path β can be shut off under a state in which the connection member 15 is connected to the collection port 12. As such, it is possible to surely prevent outflow of fluid from the discharge path β when fluid is extracted from the collection port 12 through the connection member 15 and accordingly it is possible to more favorably flow extracted fluid to the connection line L3.

Similarly to the first embodiment, correction portions (tapered portions 13d, 13e) are also formed in the second embodiment on the inner circumference of the outer circumference wall part 13 for correcting position (radial position) and attitude (inclination) of the connection member 15 relative to the collection port 12 before a tip end 15c of the connection member 15 reaches the projected end 12a of the collection port 12 during insertion process (connection process) of the connection member 15 into the outer circumference wall part 13.

Similarly to the first embodiment, the correction portion comprises the tapered portion 13d formed on the inner circumference of the outer circumference wall part 13 at a position outer side (right side in FIG. 11) of the projected end 12a of the collection port 12 and the tapered portion 13e formed on an opening edge of the outer circumference wall part 13. These tapered portions 13d, 13e are adapted to be abutted respectively by the tip end 15c and the fitting portion 16 of the connection member 15 during the inserting process (connection process) of the connection member 15 to the outer circumference wall part 13 (i.e. to the collection port 12).

If the position or attitude of the connection member 15 relative to the collection port 12 is deviated each other during connection of the connection member 15 to the outer circumference wall part 13, the tip end 15*c* of the connection member 15 will be abutted against the tapered portion 13*d* (see FIG. 7) and the fitting portion 16 will be abutted against the tapered portion 13*e* (see FIG. 8). Accordingly, the deviation of the position or attitude of the connection member 15 relative to the collection port 12 can be corrected. On the other hand, if the position or attitude of the connection member 15 relative to the collection port 12 is not deviated each other, no abutment against the tapered portions 13*d*, 13*e* is caused.

In addition, also in the dialysate extraction device of the second embodiment, a length La (FIG. 4) between the projected end 12*a* of the collection port 12 and a tip end 13*c* of the outer circumference wall part 13 is substantially same as or larger than a length Lb (FIG. 5) between the tip end 15*c* of the connection member 15 and the fitting portion 16 (max. diameter portion) of the connection member 15 (i.e. La≥Lb). This makes it possible to commence the fitting of the fitting portion (seal member) 16 before the tip end 15*c* of the connection member 15 reaches the projected end 12*a* of the collection port 12 during connection of the connection member 15 to the collection port (or the outer circumference wall part 13).

Figure 14:
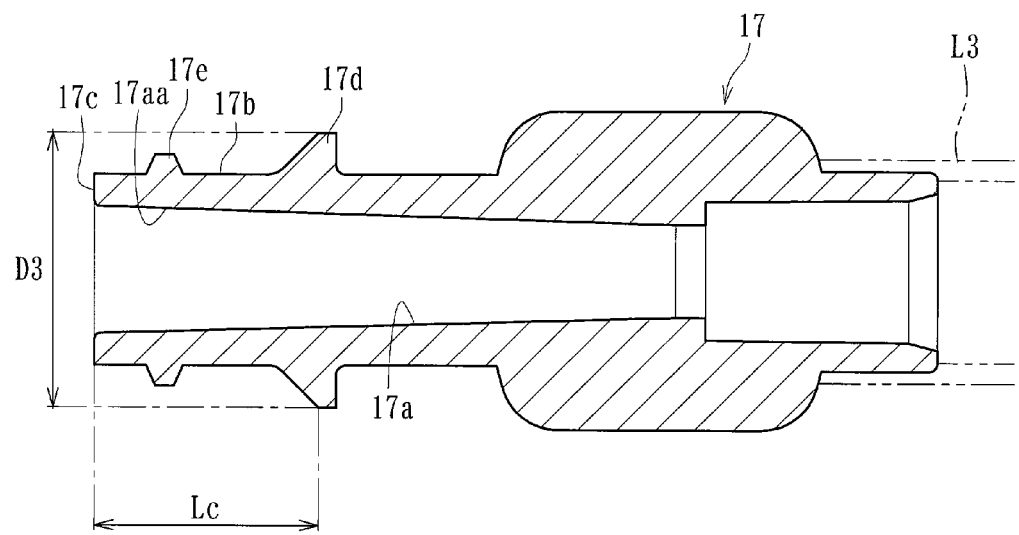
FIG. 14 A longitudinal section view showing a modified connection member used for the dialysate extraction device of the present invention.
Figure 15:
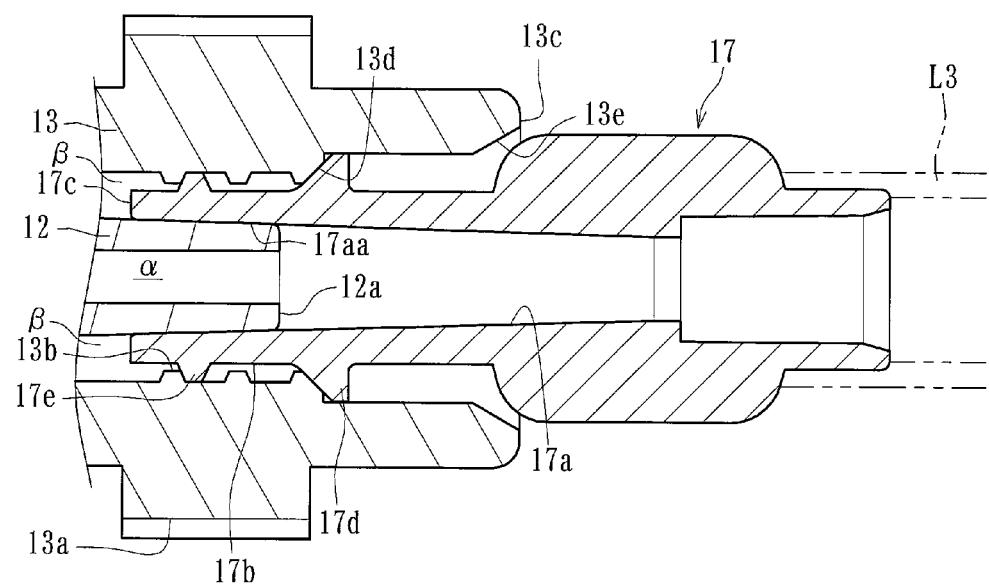
FIG. 15 A longitudinal section view showing a state in which the modified connection member of FIG. 14 has been connected to the collection port.

According to the second embodiment of the present invention, since outflow of fluid through the discharge path β can be shut off under a state in which the connection member 15 is connected to the collection port 12, a modified connection member 17 e.g. shown in FIGS. 14 and 15 may be used. The connection member 17 is formed with a male thread 17*e* on a portion projected from the outer circumference 17*b* near the tip end 17*c* which is threadably engaged with a female thread 13*b* and also formed with a fitting portion 17*d* adapted to be fitted with the inner circumference of the outer circumference wall part 13.

The fitting portion 17*d* is formed on a larger diameter portion projected from the outer circumference 17*b* and an outer diameter (max. diameter) D3 is same as or slightly larger than the inner diameter D1 (FIG. 11) of the outer circumference wall part 13 so as to be fitted to the outer circumference wall part 13. The fitting portion 17*d* may have a sealing function as the seal member or may not have such a sealing function.

Similar to the first embodiment, if the position or attitude of the connection member 17 relative to the collection port 12 is deviated each other during connection of the connection member 17 to the outer circumference wall part 13, the tip end 17*c* of the connection member 17 will be abutted against the tapered portion 13*d* and the fitting portion 17*d* will be abutted against the tapered portion 13*e*. Accordingly, the deviation of the position or attitude of the connection member 17 relative to the collection port 12 can be corrected. As shown in FIG. 15, under a condition in which the connection member 17 is completely connected to the collection port 12, the male thread 17*e* of the connection member 17 is threadably engaged with the female thread 13*b* of the outer circumference wall part 13 and the connection portion 17*aa* is closely contacted with the outer circumference of the collection port 12.

Similarly to the first embodiment, also in the second embodiment, a length La (FIG. 11) between the projected end 12*a* of the collection port 12 and a tip end 13*c* of the outer circumference wall part 13 is substantially same as or larger than a length Lc (FIG. 14) between the tip end 17*c* of the connection member 17 and the fitting portion 17*d* (max. diameter portion) of the connection member 17 (i.e. La≥Lc). This makes it possible to commence the fitting of the fitting portion 17*d* before the tip end 17*c* of the connection member 17 reaches the projected end 12*a* of the collection port 12 during connection of the connection member 17 to the outer circumference wall part 13.

According to the first and second embodiments of the present invention, since correction portions (tapered portion 13*d*, 13*e*) are formed on the inner circumference of the outer circumference wall part 13 for correcting position and attitude of the connection member 15, 17 relative to the collection port 12 before a tip end 15*c*, 17*c* of the connection member 15, 17 reaches the projected end 12*a* of the collection port 12 during insertion of the connection member 15, 17 into the outer circumference wall part 13, it is possible to surely keep the cleanliness of the collection port 12 during connection of the connection member 15, 17 to the collection port 12.

In addition, since a length La between the projected end 12*a* of the collection port 12 and a tip end 13*c* of the outer circumference wall part 13 is substantially same as or larger than a length Lb, Lc between the tip end 15*c*, 17*c* of the connection member 15, 17 and the fitting portion of the connection member 15, 17, it is possible to correct position and attitude of the connection member 15, 17 relative to the collection port 12 before a tip end 15*c*, 17*c* of the connection member 15, 17 reaches the projected end 12*a* of the collection port 12 and thus to surely keep the cleanliness of the collection port 12 during connection of the connection member 15, 17 to the collection port 12.

Furthermore, since the correction portions are formed as tapered portions 13*d*, 13*e* formed on the inner circumference of the outer circumference wall part 13, it is possible to smoothly and surely correct position and attitude of the connection member 15, 17 relative to the collection port 12 before a tip end 15*c*, 17*c* of the connection member 15, 17 reaches the projected end 12*a* of the collection port 12. Especially, if the fitting portion 16, 17*d* of the connection member 15, 17 comprises a seal member, leak of fluid can be effectively prevented even if connection of the connection member 15, 17 relative to the collection port 12 is not correctly performed.

In addition, since the collection port 12 forms a guide path α for guiding the fluid introduced through the inlet port 9*a* toward the projected end 12*a* of the collection port 12 and a discharge path β for discharging the fluid guided by the guide path α toward the outlet port 9*b* under a condition in which the cap (open/close member) 10 is mounted on the outer circumference wall part 13, it is possible to flow flushing water or disinfection liquid through the guide path α and discharge path β and to surely perform flushing and disinfection of the inside of the collection port 12. In addition, since the collection port 12 has both the functions of collection of fluid and of definition of the guide path α and discharge path β, simplification of structure can be attained with eliminating any other definition means.

In addition, since the cap (open/close member) 10 is provided with a seal member 11 for sealing between the outer circumference or the tip end face of the outer circumference wall part 13 and the open/close member 10, it is possible to more surely define the guide path α and the discharge path β under a condition in which the open/close member 10 is mounted on the collection port 12 and thus to more effectively perform flow of the flushing water and disinfection liquid. Furthermore, according to the present invention, it is possible to provide a blood purification apparatus which can keep cleanliness of the collection port 12 during connection of the connection member 15, 17 to the collection port 12 when the present invention is applied to a blood purification apparatus. Furthermore, it is possible to provide a connection line L3 which can keep cleanliness of the collection port 12 during connection of the connection member 15, 17 to the collection port 12.

Since guide path α is formed inside the collection port 12 and the discharge path β is formed between the outer circumference of the collection port 12 and the inner circumference of the outer circumference wall part 13, it is possible to smoothly flow washing water or disinfection liquid through the guide path α and the discharge path β. In addition, since the dialysate extraction means 9 is provided with the pressure-difference generation part 14 for increasing the pressure of fluid flowing toward the guide path α higher than that of fluid flowing toward the outlet port 9b, of fluid introduced from the inlet port 9a, it is possible to more surely flow washing water or disinfection liquid to the guide path α and the discharge path β by a pressure-difference generated by the pressure-difference generating part 14.

Especially, since the pressure-difference generation part 14 comprises the flow passage 14a of fluid flowing from the inlet port 9a to the collection port opening and is formed by the tapered surface reducing its diameter toward the collection port opening, it is possible to increase pressure of fluid flowing from the inlet port 9a to the guiding path α higher than that of fluid flowing from the inlet port 9a to the discharge port 9b and thus to surely flow the washing water or disinfection liquid to the guide path α and the discharge path β.

Finally although it is described preferable embodiments of the present invention, the present invention is not limited to these embodiments. For example, the collection port is not limited to that defining the guide path α and the discharge path β and it may be a structure having a simply formed projection to which a connection member can be connected to extract fluid. In addition, the correction portions are not limited to the tapered portions 13d, 13e and may be any type of structure which is able to correct relative position and attitude of the connection member relative to the collection port before the tip end of the connection member reaches the projected end of the collection port. Furthermore, the correction portion may be formed by either one of the tapered portions 13d or 13e.

In addition, the open/close member may be a member other than a cap and the pressure-difference generate part may be omitted. Furthermore, the blood purification apparatus to which the dialysate extraction device is applied may be any type of apparatus e.g. one introducing and discharge dialysate by a chamber in place of the duplex pump 7 and one using other type of blood purification instrument in place of the dialyzer 1. In addition, although it is described that the dialysate extraction device is connected to the dialysate introduction line L1, it may be connected to other flow path in a main body of a dialysis apparatus than the dialysate introduction line L1.

APPLICABILITY IN INDUSTRIES

The present invention can be applied to any other dialysate extraction device having a different appearance or other additional functions if the dialysate extraction device is provided with correction portions formed on the inner circumference of the outer circumference wall part for correcting position and attitude of the connection member relative to the collection port before a tip end of the connection member reaches the projected end of the collection port during insertion of the connection member into the outer circumference wall part.

EXPLANATION OF REFERENCE NUMERALS 1 dialyzer (blood purification instrument)
2 arterial blood circuit
3 venous blood circuit
4 blood pump
5 arterial air trap chamber
6 venous air trap chamber
7 duplex pump
8 ultrafiltration pump
9 dialysate extraction means
10 cap (open/close member)
11 seal member
12 collection port
13 outer circumference wall part
13d, 13e tapered portion (correction portion)
14 pressure-difference generation part
15 connection member
16 fitting portion (seal member)
17 connection member
17d fitting portion

What is claimed is:

1. A dialysate extraction device comprising:
   a) a dialysate extraction means including:
      i) an inlet port;
      ii) an outlet port, wherein the inlet port and the outlet port are adapted to be connected to a flow path of fluid for flowing the fluid therethrough; and
      iii) a projected collection port including a projected end, wherein the projected collection port is configured for collecting the fluid flowing through the inlet port and the outlet port;
   b) an outer circumference wall part mounted on the dialysate extraction means so that the outer circumference wall part covers the projected end of the projected collection port and is projected therefrom;
   c) a connection member including:
      i) a connection portion, wherein the connection portion is adapted to be connected to the projected collection port; and
      ii) a fitting portion that is adapted to be fitted into an inner circumference of the outer circumference wall part; and
   the connection member is adapted to extract the fluid from the collection port under a condition in which the connection portion is connected to the outer circumference wall part;
   d) correction portions formed on the inner circumference of the outer circumference wall part, wherein the correction portions correct position and attitude of the connection member relative to the projected collection port before a tip end of the connection member reaches the projected end of the projected collection port during insertion of the connection member into the outer circumference wall part.

2. The dialysate extraction device of claim 1, wherein a length between the projected end of the projected collection port and a tip end of the outer circumference wall part is substantially same as or larger than a length between the tip end of the connection member and the fitting portion of the connection member.

3. The dialysate extraction device of claim 1, wherein the correction portions are formed as tapered portions formed on the inner circumference of the outer circumference wall part.

4. The dialysate extraction device of claim 1, wherein the fitting portion of the connection member comprises a seal member for sealing between the outer circumference of the connection member and the inner circumference of the outer circumference wall part.

5. The dialysate extraction device of claim 1, wherein the dialysis extraction device further comprises an open/close member detachably mounted on the outer circumference wall part for opening and closing the projected collection port, and wherein the projected collection port forms a guide path for guiding the fluid introduced through the inlet port toward the projected end of the projected collection port and a discharge path for discharging the fluid guided by the guide path toward the outlet port under a condition in which the open/close member is mounted on the outer circumference wall part.

6. The dialysate extraction device of claim 5, wherein the open/close member is provided with a seal member for sealing between the outer circumference or the tip end face of the outer circumference wall part and the open/close member.

7. A blood purification apparatus comprising the dialysate extraction device of claim 1.

8. A connection line having a tip end to which the connection member of claim 1 is connected.

9. The dialysate extraction device of claim 2, wherein the correction portions are formed as tapered portions formed on the inner circumference of the outer circumference wall part.

10. The dialysate extraction device of claim 2, wherein the fitting portion of the connection member comprises a seal member for sealing between the outer circumference of the connection member and the inner circumference of the outer circumference wall part.

11. The dialysate extraction device of claim 3, wherein the fitting portion of the connection member comprises a seal member for sealing between the outer circumference of the connection member and the inner circumference of the outer circumference wall part.

12. The dialysate extraction device of claim 2, wherein the dialysis extraction device further comprises an open/close member detachably mounted on the outer circumference wall part for opening and closing the projected collection port, and wherein the projected collection port forms a guide path for guiding the fluid introduced through the inlet port toward the projected end of the projected collection port and a discharge path for discharging the fluid guided by the guide path toward the outlet port under a condition in which the open/close member is mounted on the outer circumference wall part.

13. The dialysate extraction device of claim 4, wherein the dialysis extraction device further comprises an open/close member detachably mounted on the outer circumference wall part for opening and closing the projected collection port, and wherein the projected collection port forms a guide path for guiding the fluid introduced through the inlet port toward the projected end of the projected collection port and a discharge path for discharging the fluid guided by the guide path toward the outlet port under a condition in which the open/close member is mounted on the outer circumference wall part.

14. The dialysate extraction device of claim 11, wherein the dialysis extraction device further comprises an open/close member detachably mounted on the outer circumference wall part for opening and closing the projected collection port, and wherein the projected collection port forms a guide path for guiding the fluid introduced through the inlet port toward the projected end of the projected collection port and a discharge path for discharging the fluid guided by the guide path toward the outlet port under a condition in which the open/close member is mounted on the outer circumference wall part.

15. A blood purification apparatus comprising the dialysate extraction device of claim 2.

16. A blood purification apparatus comprising the dialysate extraction device of claim 3.

17. A blood purification apparatus comprising the dialysate extraction device of claim 14.

18. A connection line having a tip end to which the connection member of claim 2 is connected.

19. A connection line having a tip end to which the connection member of claim 13 is connected.

20. A connection line having a tip end to which the connection member of claim 17 is connected.

* * * * *